United States Patent [19]
Gutterer

[11] Patent Number: 5,728,826
[45] Date of Patent: Mar. 17, 1998

[54] SILYL COMPOUNDS AND THEIR USE

[75] Inventor: Beate Gutterer, Allensbach, Germany

[73] Assignee: Byk Gulden Lomberg Chemische Fabrik GmbH, Constance, Germany

[21] Appl. No.: 704,574

[22] PCT Filed: Mar. 7, 1995

[86] PCT No.: PCT/EP95/00836

§ 371 Date: Nov. 25, 1996

§ 102(e) Date: Nov. 25, 1996

[87] PCT Pub. No.: WO95/24416

PCT Pub. Date: Sep. 14, 1995

[30] Foreign Application Priority Data

Mar. 9, 1994 [CH] Switzerland ............... 00701/94

[51] Int. Cl.$^6$ .................................. C07J 71/00
[52] U.S. Cl. ................................ 540/61; 552/505
[58] Field of Search .................. 552/505; 540/61

[56] References Cited

U.S. PATENT DOCUMENTS 3,513,163  5/1970  Brown ..................... 260/239.55
5,482,934  1/1996  Calatayud et al. ............ 514/174

Primary Examiner—Matthew V. Grumbling
Assistant Examiner—Michael Bucknum
Attorney, Agent, or Firm—Jacobson, Price, Holman & Stern, PLLC

[57] ABSTRACT

The invention describes a process for the epimer enrichment of compounds of formula (I) by silation, fractionated crystallization and acid hydrolysis.

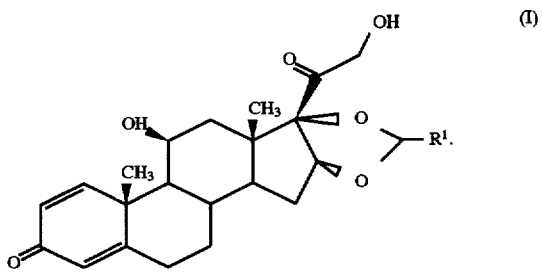

10 Claims, 1 Drawing Sheet (I)

(II)

SILYL COMPOUNDS AND THEIR USE

FIELD OF THE INVENTION

The invention relates to novel silyl compounds and their use in the synthesis of active compounds which are used in the pharmaceutical industry for the preparation of drugs.

KNOWN TECHNICAL BACKGROUND

U.S. Pat. No. 3,513,163 discloses 21-trialkylsiloxypregnane derivatives, which are said to have anti-inflammatory and gluconeogenic properties. DE-OS 41 29 535 discloses pregna-1,4-diene-3,20-dione 16,17-acetal-21-esters, which bear a butyl, isopropyl, sec-butyl, cyclohexyl or phenyl radical on the cyclic acetal ring, and whose C-21hydroxyl group is acylated by an acetyl or isobutyryl radical.

SUMMARY OF THE INVENTION

In the case of chiral active compounds, one enantiomer or one epimer is frequently more active or linked with fewer side effects than the other. Obtaining the desired enantiomer or epimer as selectively as possible and as pure as possible is therefore of great importance in the case of chiral active compounds.

According to the invention, a novel process is now provided by which the epimers of certain pregna-1,4-diene-3,20-dione derivatives may be separated particularly effectively.

DETAILS

Figure 1:
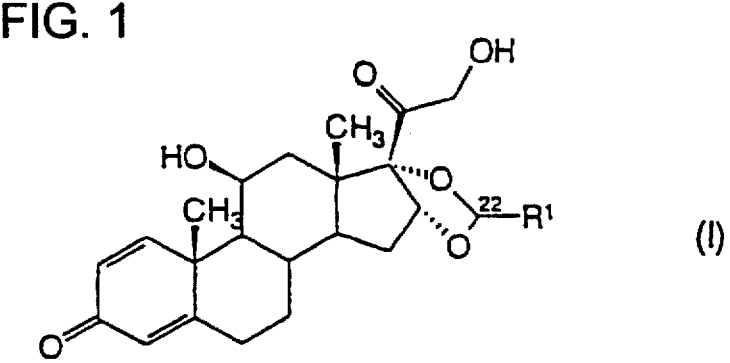
FIGS. 1 and 2 present structural formulae I and II, respectively.
Figure 2:
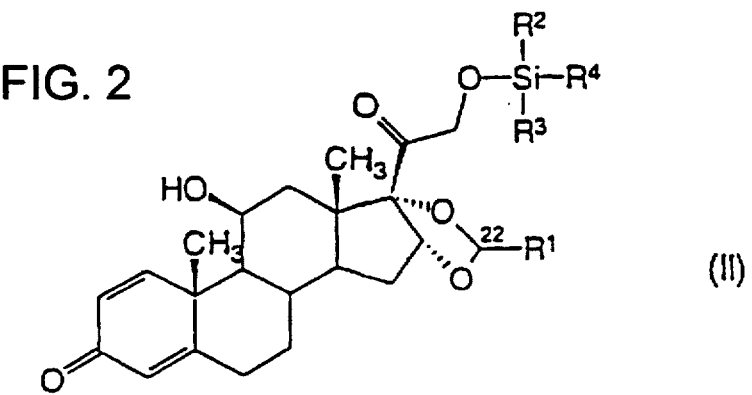

The invention relates to a process for enriching the R-epimer in an R/S epimer mixture of compounds of the formula I (see FIG. 1), in which R1 denotes 1–7C-alkyl or 3–8C-cycloalkyl, which is characterized in that the R/S epimer mixture of the compounds of the formula I is silylated with compounds X-Si(R2) (R3)R4, in which R2, R3 and R4 are identical or different and each signifies a 1–7C-alkyl radical or phenyl radical and X signifies a suitable leaving group, the resulting R/S mixture of the silyl derivative of the formula II (see FIG. 2), in which R1, R2, R3 and R4 have the meanings given above, is fractionally crystallized, and the R-epimer-enriched R/S-epimer mixture of compounds of the formula I is released by acid hydrolysis from the crystal fractions obtained first.

1–7C-Alkyl represents straight-chain or branched alkyl radicals having 1 to 7 carbon atoms. Those which may be mentioned by way of example are the heptyl, hexyl, neopentyl, isopentyl, pentyl, butyl, isobutyl, sec-butyl, tert-butyl, propyl, isopropyl, ethyl and the methyl radical.

A preferred 1–7C-alkyl radical R1 is the propyl radical.

A preferred 1–7C-alkyl radical R2 is the methyl radical.

A preferred 1–7C-alkyl radical R3 is the methyl radical.

A preferred 1–7C-alkyl radical R4 is the 1,1,2-trimethylpropyl radical (thexyl radical).

3–8C-cycloalkyl represents the cyclopropyl, cyclobutyl, cyclopentyl, cyclohexyl, cycloheptyl and cyclooctyl radical. A preferred 3–8C-cycloalkyl radical is the cyclohexyl radical.

The reaction of the compounds of the formula I with the silyl compounds X-Si(R2) (R3)R4 is performed in a manner known to those skilled in the art in inert solvents, as, for example, in dimethylformamide, chloroform, methylene chloride, diethyl ether, tetrahydrofuran or pyridine at temperatures between 20° C. and 80° C., in particular between 40° C. and 60° C. Suitable leaving groups X which may be mentioned are preferably halogen atoms, in particular chlorine.

The reaction is preferably performed in the presence of an auxiliary base, for example in the presence of an inorganic carbonate, such as potassium carbonate, or in the presence of a suitable organic amine, such as triethylamine, diisopropylethylamine, pyridine or imidazole.

The fractional crystallization is performed in a manner known to those skilled in the art, for example by gradual concentration of the solution in whose solvent the R-epimer is less soluble than the S-epimer, and separating off the precipitating crystals, or by gradual addition of a solvent to a solution in which the R-epimer is less soluble than the S-epimer, and separating off the precipitating crystals. Solvents in which the R-epimer of the compounds of the formula II is less soluble than the S-epimer which may be mentioned by way of example are: esters, such as ethyl acetate or ethyl acetate/petroleum ether mixtures; alcohols, such as ethanol or ethanol/water mixtures.

By means of this fractional crystallization, which, if desired, can also be repeated, according to the invention the R-epimer may be enriched to >97%, in particular to >99%.

The acid hydrolysis of the compounds of the formula II (elimination of the Si(R2) (R3)R4 radical) is performed in a manner known per se in aqueous or water-containing solvents, such as tetrahydrofuran or dimethylformamide in the presence of an acid, such as trifluoroacetic acid, acetic acid or hydrogen chloride, the molar ratio of acid/compound II advantageously being between 1:1 and 10:1 and the molar ratio of water/compound II being between 5:1 and 20:1. Surprisingly, in the acid hydrolysis of the silyl radical, the acetal ring is not attacked.

To carry out the process of the invention, advantageously, one starts from those compounds of the formula I in which the R-epimer is already enriched. The compounds of the formula I are obtained in this case in a manner known per se by reacting 16-hydroxyprednisolone with the corresponding aldehyde R1-CHO, the reaction being able to be controlled by suitable variation of the reaction conditions in such a manner that the R-epimer is predominantly formed. For the predominant preparation of the R-epimer of the formula I, for example, the following conditions are preferred: halogenated hydrocarbons or nitromethane containing methanesulphonic acid at room temperature to 40° C., or 35–70% strength perchloric acid at 0° C. to room temperature. Another possibility for the predominant preparation of the R-epimer is treatment of the epimer mixture (formula I) with 70% strength perchloric acid in a suitable solvent, such as, e.g., methylene chloride, at 0° C. (epimerization).

The invention further relates to the compounds of the formula II, in which R1, R2, R3 and R4 have the meanings given above.

The following examples describe the invention in more detail. RT represents room temperature, min. represents minute(s), h represents hour(s), m.p. represents melting point.

EXAMPLES

A. Preparation of the compounds II

1. Compound IIa ($R^1$=cyclohexyl, $R^2$=$R^3$=$R^4$=methyl)

3.0 g (6.37 mmol) of the compound I where $R^1$=cyclohexyl are dissolved in 15 ml of dimethylformamide, admixed with 510 mg (7.5 mmol) of imidazole and 980 mg (9.0 mmol) of trimethylchlorosilane and stirred for 30 min. at RT. The mixture is poured onto sodium hydrogen carbonate solution, the solid is filtered off by suction and rinsed with water. Crude yield quantitative, $R_f$=0.66 (silica gel, ethyl acetate/petroleum ether=2:3).

2. Compound IIb ($R^1$=cyclohexyl, $R^3$=$R^4$=methyl, $R^2$=thexyl)

10.0 g (21.2 mmol) of the compound I where $R^1$=cyclohexyl are dissolved in 60 ml of dimethylformamide, admixed with 2.0 g (29.4 mmol) of imidazole and 5.0 ml (25.4 mmol) of thexyldimethylsilyl chloride. After stirring for 2 h at 30°–40° C., the mixture is poured into 400 ml of 0.5N hydrochloric acid, the precipitate is filtered off with suction and rinsed with water. Crude yield: quantitative. $R_f$(22R)=0.6, $R_f$(22S)=0.56 (silica gel, petroleum ether/ethyl acetate=2:1).

3. Compound IIb ($R^1$=cyclohexyl, $R^3$=$R^4$=methyl, $R^2$=thexyl)

0.77 g (1.64 mmol) of the compound I where $R^1$=cyclohexyl are dissolved in 10.0 ml of pyridine and admixed with 0.45 g (2.5 mmol) of thexyldimethylchlorosilane and 10.0 mg of dimethylaminopyridine. The mixture is heated at 80° C. for 6 h, and poured into water and the water phase is extracted with ethyl acetate. The organic phase is washed in 1N hydrochloric acid, dried with sodium sulphate, filtered off with suction, admixed with hexane and slowly concentrated in vacuo. The precipitate is filtered off with suction and dried. Yield 0.22 g (22%); $R_f$ value, see Example 2.

4. Compound IIb ($R^1$=cyclohexyl, $R^3$=$R^4$=methyl, $R^2$=thexyl)

5 g (10.6 mmol) of the compound I where $R^1$=cyclohexyl are dissolved in 30 ml of dimethylformamide and admixed with 9.6 g (53.7 mmol) of thexyldimethylchlorosilane. At 60° C., 4.5 g (32.6 mmol) of potassium carbonate are added in portions. After stirring for 6 h, the mixture is extracted with water/ethyl acetate and the organic phase, after drying with sodium sulphate, is concentrated. The residue is washed by stirring with 20 ml of isopropanol, filtered off with suction and dried. Yield: 4.8 g (74%); $R_f$ value, see Example 2.

5. Compound IIc ($R^1$=cyclohexyl, $R^2$=$R^3$=$R^4$=isobutyl)

5.0 g (10.6 mmol) of the compound I where $R^1$=cyclohexyl are dissolved in 25 ml of dimethylformamide and admixed with 1.0 g (14.7 mmol) of imidazole and 3.08 g (13.1 mmol) of triisobutylchlorosilane. After stirring for 5 h, the solution is poured dropwise into water, extracted with ethyl acetate, the organic phase is dried with sodium sulphate and concentrated. Crude yield 93%, $R_f$=0.71 (silica gel, petroleum ether/ethyl acetate=3:2).

6. Compound IId ($R^1$=cyclohexyl, $R^3$=$R^4$=methyl, $R^2$=t-butyl)

10.0 g (21.3 mmol) of the compound I where $R^1$=cyclohexyl are dissolved in 60 ml of dimethylformamide and admixed with 1.7 g (25.0 mmol) of imidazole and 3.77 g (25.0 mmol) of t-butyldimethylchlorosilane. After stirring for 3 h at RT, the mixture is poured into water, the precipitate is filtered off with suction and washed with water. Crude yield 95%, $R_f$=0.76 (silica gel, ethyl acetate/petroleum ether=2:3).

7. Compound IIe ($R^1$=cyclohexyl, $R^2$=t-butyl, $R^3$=$R^4$=phenyl)

4.7 g (10.0 mmol) of the compound I where $R^1$=cyclohexyl are dissolved in 25 ml of dimethylformamide and admixed with 885 mg (13.0 mmol) of imidazole and 3.3 g (12.0 mmol) of t-butyldiphenylchlorosilane. After stirring for 4 h at RT, the solution is poured dropwise into water, the precipitate is filtered off with suction, washed with water and dried. Crude yield: 6.4 g (91%); $R_f$=0.55 (silica gel, petroleum ether/ethyl acetate=3:2).

8. Compound IIf ($R^1$=propyl, $R^2$=thexyl, $R^3$=$R^4$=methyl)

9.0 g (20.9 mmol) of the compound I where $R^1$=propyl and 1.77 g (26.0 mmol) of imidazole are dissolved in 50 ml of dimethylformamide and admixed with 4.47 ml (25.0 mmol) of thexyldimethylchlorosilane. After stirring for 20 min. at 40° C., the solution is poured dropwise into 1 l of water, the precipitate is filtered off with suction and dried. Crude yield: quantitative. $R_f$=0.74 (silica gel, ethyl acetate/petroleum ether=1:1).

B. Epimer enrichment in the compounds II 9. 1.5 g (2.76 mmol) IIa ($R^1$=cyclohexyl; $R^2$=$R^3$=$R^4$=methyl, 92% 22 R epimer) are dissolved warm in 5 ml of ethyl acetate and admixed with petroleum ether until the onset of turbidity. The crystals are filtered off with suction and dried. Yield: 0.56 g (37%), m.p. 176°–179° C., 96% 22R epimer. $R_f$ value, see Example 1.

10. 11.8 g (20.2 mmol) of IId ($R_1$=cyclohexyl, $R^2$=t-butyl, $R^3$=$R^4$=methyl, 91% 22R epimer) are dissolved in ethyl acetate and slowly concentrated in vacuo. The precipitate is filtered off with suction and dried. Yield: 4.42 g (37.5%), 98.6% 22R epimer. M.p.: 238°–241° C., $R_f$ value, see Example 6.

11. 396 g (646 mmol) of IIb ($R^1$=cyclohexyl, $R^2$=thexyl, $R^3$=$R^4$=methyl, 92.5% 22R epimer) are dissolved in 5.0 l of ethyl acetate with heating, and slowly concentrated in vacuo. The resulting suspension is filtered off with suction and dried. Yield: 317 g (80%), 98% 22R epimer. M.p.: 237°–243° C., $R_f$ value, see Example 2.

12. 13.0 g (21.2 mmol) of IIb ($R^1$=cyclohexyl, $R^2$=thexyl, $R^3$=$R^4$=methyl, 91% 22R epimer) are recrystallized in 200 ml of absolute ethanol. Yield: 8.4 g (64.6%), 97% 22R epimer. M.p.: 232°–238° C., $R_f$ value, see Example 2).

13. 3.0 g (4.9 mmol) of IIb ($R^1$=cyclohexyl, $R^2$=thexyl, $R^3$=$R^4$=methyl, 93% 22R epimer) are extracted hot with 20 ml of ethyl acetate. Yield: 2.02 g (3.29 mmol, 67.3), 99.3% 22R epimer. M.p.: 240°–243° C., $R_f$ value, see Example 2.

14. 3.0 g (4.9 mmol) of IIb ($R^1$=cyclohexyl, $R^2$=thexyl, $R^3$=$R^4$=methyl, 93% 22R epimer) are extracted hot with 20 ml of ethanol. Yield: 2.43 g (3.96 mmol, 81.0), 97.5% 22R epimer. M.p.: 241°–243° C., $R_f$ value, see Example 2.

15. 10.0 g (17.46 mmol) of IIf ($R^1$=propyl, $R^2$=thexyl, $R^3$=$R^4$=methyl, 82% 22R epimer) are recrystallized in 22 ml of ethanol. Yield: 5.81 g (10.1 mmol, 58.1%), approximately 92% 22R epimer. M.p.: 220°–223° C., $R_f$ value, see Example 7.

C. Acid hydrolysis of the compounds II 16. 16.6 g (27.1 mmol) of IIb ($R^1$=cyclohexyl, $R^2$=thexyl, $R^3$=$R^4$=methyl, ≧99% 22R epimer) are dissolved in 65 ml of tetrahydrofuran, admixed with 4.6 g (40.5 mmol) of trifluoroacetic acid and 3 ml of water and stirred for 12 h at 60° C. 3.5 g of solid sodium hydrogen carbonate are added, the mixture is filtered off with suction and the filtrate is concentrated. The residue is dissolved in ethyl acetate and slowly concentrated in vacuo, the precipitate is filtered off with suction and dried. Yield 11.0 g of the compound I where $R^1$=cyclohexyl (86.2%). M.p.: 256°–261° C. (hot extraction with ethyl acetate). 99.4% 22R epimer. $R_f$=0.21 (silica gel, ethyl acetate/petroleum ether=1:1).

17. 5.0 g (8.2 mmol) of IIb ($R^1$=cyclohexyl, $R^2$=thexyl, $R^3$=$R^4$=methyl, ≧98% 22R epimer) are suspended in 15 ml of dimethylformamide, admixed with 1.14 g (13 mmol) of trifluoroacetic acid and 2 ml of water and, after stirring for 6.5 h at 50° C., 1.1 g (13 mmol) of sodium hydrogen carbonate is added. The solution is poured dropwise into water, the precipitate is filtered off with suction, washed with water and dried. Yield 3.75 g (97%) of the compound I where $R^1$=cyclohexyl; ≧98% 22R epimer, $R_f$ value, see Example 16.

18. 20 g of IIb ($R^1$=cyclohexyl, $R^2$=thexyl, $R^3$=$R^4$= methyl, ≧98% 22R epimer) are dissolved in 500 μl of tetrahydrofuran, admixed with 500 μl of acetic acid and 200 μl of water, and stirred for 4 h at 40° C. and 12 h at room temperature. Complete conversion by TLC, $R_f$ value, see Example 16, 98.5% 22R epimer.

19. 20 mg of IIb ($R^1$=cyclohexyl, $R^2$=thexyl, $R^3$=$R^4$= methyl, ≧98% 22R epimer) are dissolved in 1.0 ml of tetrahydrofuran and admixed with 50 μl of 14% strength hydrogen chloride/dioxane solution. The mixture is stirred for 3 h at room temperature and is then neutralized with sodium hydrogen carbonate. Conversion complete by TLC, $R_f$ value, see Example 16, 98.7% 22R epimer.

20. 0.5 g (0.85 mmol) of IId ($R^1$=cyclohexyl, $R^2$=t-butyl, $R^3$=$R^4$=methyl, ≧97.5% 22R epimer) are dissolved in 2 ml of tetrahydrofuran and admixed with 200 μl (2.6 mmol) of trifluoroacetic acid and 100 μl of water. After stirring for 1 h at 70° C., the solution is concentrated, the residue is suspended in diisopropyl ether, filtered off with suction and dried. Yield: 0.32 g (80%) of the compound I where $R^1$=cyclohexyl; 97% 22R epimer, $R_f$ value, see Example 16.

21. 3.2 g (5.59 mmol) of IIf ($R^1$=propyl, $R^2$=thexyl, $R^3$=$R^4$=methyl, ≧97% 22R epimer) are dissolved in 20 ml of tetrahydrofuran and admixed with 1.0 g (9.0 mmol) of trifluoroacetic acid and 600 μl of water. The mixture is stirred for 10 h at 65° C. and for 10 h at RT, 840 mg (10 mmol) of sodium hydrogen carbonate are added and the procedure as specified under Example 16 is followed. Yield: 1.6 g (66.5%) of the compound I where $R^1$=propyl. M.p.: 264°–267° C. (hot extraction ethanol), 97.8% 22R epimer. $R_f$=0.19 (silica gel, ethyl acetate/petroleum ether=1:1).

D. Preparation of the starting compounds I 22. 9.4 g (25 mmol) of 16α-hydroxyprednisolone are suspended in 70 ml of nitromethane, admixed, with cooling in an ice bath, with 6.87 ml (80 mmol) of 70% strength perchloric acid, and 2.16 g (30 mmol) of butyraldehyde are added dropwise. After stirring for 16 h at RT, the mixture is poured into sodium hydrogen carbonate solution, the precipitate is filtered off with suction, washed with water and dried at 60° C. in vacuo. Yield: 10.0 g (92%), epimer ratio R/S=82/18.

23. 2.0 g (5.3 mmol) of 16α-hydroxyprednisolone are suspended in 10 ml of nitromethane and 1.5 ml (17.4 mmol) of 50% strength perchloric acid and then 0.8 ml (6.6 mmol) of cyclohexanealdehyde are added dropwise. After stirring for 2 h at RT, the reaction mixture is admixed with sodium hydrogen carbonate solution, the precipitate is filtered off with suction, washed with water and dried at 50° C. in a high vacuum. Yield: 2.2 g (88%), epimer ratio R/S=92/8.

Determination of the epimer ratios for compounds I and II

The epimer ratios are determined by HPLC. In the determination, compounds IIa–e must be converted to the corresponding compounds I in analytical quantities according to one of the methods described in Examples 16–20, and then their epimer ratio must be determined. In the determination, different cleavage conditions lead to identical results.

Chromatographic conditions:

Phase: ODS-Hypersil, 5 μm, d=4.6 mm, l=12.5 cm

Flow rate: 1 ml/min

Room temperature

Compound I where $R^1$=cyclohexyl: eluent water/ethanol= 53/47

Compound I where $R^1$=propyl: eluent water/ethanol=65/ 35

Compound IIf: eluent water/ethanol=36/64

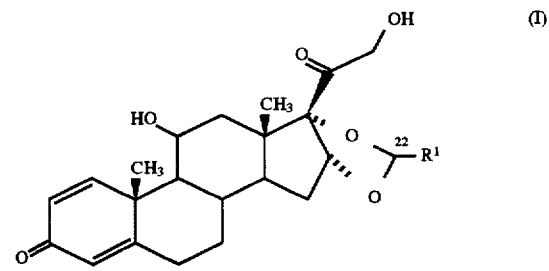

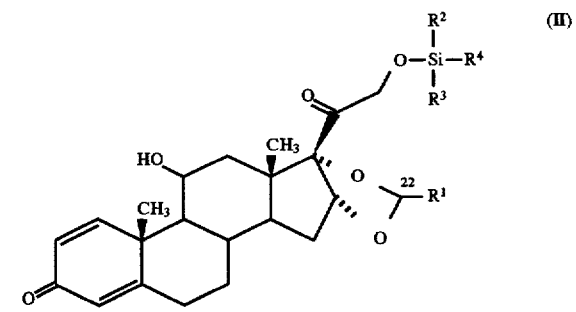

I claim:

1. A process for enriching the R epimer in an R/S epimer mixture of compounds of the formula I,

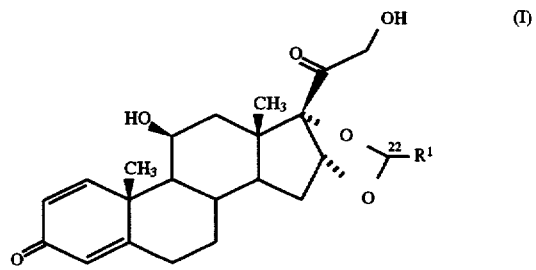

in which R1 denotes 1–7C-alkyl or 3–8C-cycloalkyl, characterized in that the R/S epimer mixture of the compounds of the formula I is silylated with compounds X-Si(R2)(R3)R4, in which R2, R3 and R4 are identical or different and each signifies a 1–7C-alkyl radical or phenyl radical and X signifies a suitable leaving group, the resulting R/S mixture of the silyl derivative of the formula II

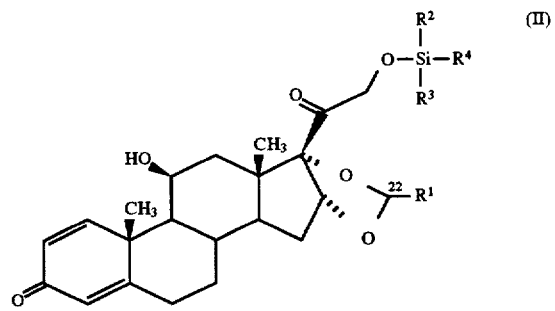

in which R1, R2, R3 and R4 have the meanings given above, is fractionally crystallized, and the R-epimer-enriched R/S- epimer mixture of compounds of the formula I is released by acid hydrolysis from the crystal fractions obtained first.

2. A process according to claim 1, in which

R1 denotes propyl or cyclohexyl,

R2 denotes methyl, isobutyl, t-butyl or thexyl,

R3 denotes methyl, isobutyl or phenyl,

R4 denotes methyl, isobutyl or phenyl and

X signifies halogen.

3. A process according to claim 1, in which

R1 denotes cyclohexyl,

R2 denotes thexyl,

R3 denotes methyl,

R4 denotes methyl and

X signifies chlorine.

4. A process according to claim 1, the fractional crystallization being performed in a solvent or solvent mixture such as ethyl acetate, ethyl acetate/petroleum ether mixture, ethanol or ethanol/water mixture.

5. A process according to claim 1, the acid hydrolysis being performed in aqueous or water-containing solvents in the presence of an acid such as trifluoroacetic acid, acetic acid or hydrogen chloride.

6. A compounds of formula II

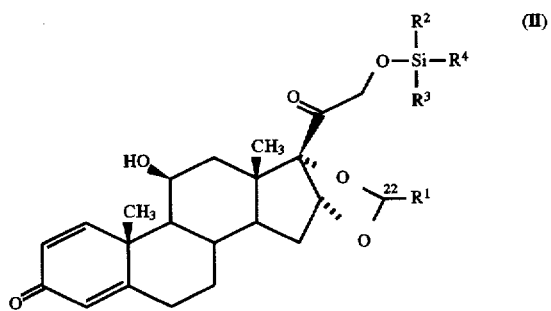

in which

R1 denotes 1–7C-alkyl or 3–8C-cycloalkyl and

R2, R3 and R4 are identical or different and each denote 1–7C-alkyl or phenyl.

7. A compounds of formula II according to claim 6 in the form of a 22R epimer.

8. A compounds of formula II according to claim 6, in which

R1 denotes propyl or cyclohexyl,

R2 denotes methyl, isobutyl, t-butyl or thexyl,

R3 denotes methyl, isobutyl or phenyl and

R4 denotes methyl, isobutyl or phenyl.

9. A compound of formula II according to claim 6, in which

R1 denotes cyclohexyl,

R2 denotes thexyl,

R3 denotes methyl and

R4 denotes methyl.

10. A compound of formula II according to claim 6, in which

R1 denotes cyclohexyl,

R2 denotes thexyl,

R3 denotes methyl and

R4 denotes methyl in the form of the 22R epimer.

* * * * *